US006631990B2

(12) United States Patent
Schippert et al.

(10) Patent No.: US 6,631,990 B2
(45) Date of Patent: Oct. 14, 2003

(54) SYSTEM FOR MEASURING DISTANCES IN THE ANTERIOR CHAMBER OF THE EYE

(75) Inventors: Manfred A. Schippert, Chelmsford, MA (US); Michael A. Chang, Weston, MA (US); Oscar K. Hollander, Falmouth, MA (US); Sheldon H. Moll, Bedford, MA (US); Gerald T. Cameron, Sr., Naples, FL (US)

(73) Assignee: Acmed, Inc., Bedford, MA (US)

( * ) Notice: Subject to any disclaimer, the term of this patent is extended or adjusted under 35 U.S.C. 154(b) by 98 days.

(21) Appl. No.: 10/024,851

(22) Filed: Dec. 19, 2001

(65) Prior Publication Data

US 2002/0085173 A1 Jul. 4, 2002

Related U.S. Application Data

(60) Provisional application No. 60/259,487, filed on Jan. 3, 2001.

(51) Int. Cl.$^7$ .................................................. A61B 3/10
(52) U.S. Cl. ........................................................ 351/214
(58) Field of Search ................................. 351/205, 206, 351/208, 214, 212, 221, 246

(56) References Cited

U.S. PATENT DOCUMENTS 5,116,114 A  * 5/1992  Nakamura et al. .......... 351/205
6,231,186 B1   5/2001  Broadus et al. ............. 351/208

* cited by examiner

Primary Examiner—George Manuel
(74) Attorney, Agent, or Firm—Weingarten, Schurgin, Gagnebin & Lebovici LLP

(57) ABSTRACT

A measurement system is provided for measuring distances in the anterior chamber of an eye in conjunction with a slit lamp ophthalmologic microscope table. The measurement system includes a linearly movable interface assembly operative to pick up motions of the microscope assembly in a direction along an optical axis of the eye. A linear measurement assembly is coupled to the interface assembly and operative to determine a distance traveled by the interface. The measurement system may further be provided with a three-axis motion assembly and an optical microscope assembly mounted on the motion assembly. An image recording device is optically aligned with the optical microscope assembly to record images from the optical microscope assembly. A controller assembly is operative to control motion of the three-axis motion assembly in a first horizontal direction parallel to an optical axis of an eye of a patient, in a second horizontal direction orthogonal to the first horizontal direction to align the microscope assembly with both eyes, and in a vertical direction. The measurement system with image recording capability may be a stand-along system or incorporated for engagement and disengagement with an existing slit lamp table.

39 Claims, 16 Drawing Sheets

SYSTEM FOR MEASURING DISTANCES IN THE ANTERIOR CHAMBER OF THE EYE

CROSS REFERENCE TO RELATED APPLICATIONS

This application claims the benefit under 35 U.S.C. §119 (e) of U.S. Provisional Application No. 60/259,487, filed on Jan. 3, 2001, the disclosure of which is incorporated by reference herein.

STATEMENT REGARDING FEDERALLY SPONSORED RESEARCH OR DEVELOPMENT

N/A

BACKGROUND OF THE INVENTION

Glaucoma is one of the leading causes of irreversible blindness worldwide. With early detection, accurate diagnosis and appropriate therapy, the visual loss of glaucoma is largely preventable. Glaucoma is not a single disease, but a large group of disorders sharing optic nerve damage as a common feature. The optic nerve damage is related to the intraocular pressure in most cases and to visual field loss in all cases.

Determination of the anatomic type of glaucoma, namely, "open angle" or "narrow or closed angle," is essential for effective treatment. Differentiation between open and narrow or closed angles must be made before a therapeutic strategy may be devised. Historically, the depth of the anterior chamber has been evaluated by the technique of gonioscopy, in which a lens is coupled to or contacts the cornea, which is uncomfortable for the patient. Direct (Koeppe) gonioscopy also requires the patient to be in a recumbent position. Gonioscopy also requires dexterity to coordinate the patient, lens, microscope and illumination source and experience to-interpret anatomic landmarks. The ancillary technique of B-scan ultrasonography has been used in recent years, but also requires contact with the corneal surface.

SUMMARY OF THE INVENTION

The present invention provides a non-invasive measurement system using optical principles to evaluate the anterior chamber depth of a patient's eye with ease, precision, and accuracy. In a first embodiment, the measurement system interfaces with an existing slit lamp ophthalmology examination table. The measurement system includes a base that mounts securely, either removably or permanently, to the slit lamp table in any suitable manner. An interface to a horizontal drive shaft of the slit lamp travels with the drive shaft in a direction, the Y direction, along the optical axis of the patient's eye, orthogonal to the axial length of the drive shaft. The interface is mounted to a linearly translatable slide mechanism coupled to a linear measurement device. Thus, as the microscope is moved in the Y direction along the optical axis of the patient's eye, the interface and the slide mechanism move the same distance.

The linear measurement device, such as a linear encoder, is in communication with suitable circuitry that is operative to translate signals from the linear measurement device to an operator-readable display. The linear measurement device and the display, such as a three- or four-digit LED display, are readily operative to indicate distances to 100 micrometer or 10 micrometer accuracy. The LED display may be set to zero at any time by pushing a suitable button in communication with the LED display.

To make a distance measurement between cornea and iris, the user first finds the location in the eye to be measured using the stereo microscope and joystick control of the slit lamp. Next, the user finds the best focus with the stereo microscope in the plane of the cornea, then pushes the zero button to zero the display. The user next moves the microscope to focus on the surface of the iris or the edge of the pupil. The distance traveled in the Y direction is detected by the measurement system and displayed for the user. The user repeats this measurement procedure on every other location within the eye required for diagnosis. Other distances within the eye may be measured, such as from the cornea to the retina or from the iris or pupil to the retina.

In a further embodiment of the present invention, the measurement system includes a three-axis stage assembly supporting an optical microscope assembly that interfaces with a digital camera and television monitor under the control of a suitably programmed controller or computer. Television frames of the eye are analyzed on the fly to store in memory unique signal signatures associated with in-focus features and their measured location between the cornea and the iris. The system may include an engagement mechanism to engage with an existing slit lamp microscope. Alternatively, the system may be configured as a stand-alone measurement system used solely for making anterior chamber distance measurements.

The present measurement system is non-invasive, requiring no contact with the eye or alteration of the configuration or distortion of the cornea or anterior chamber angle, as gonioscopy or contact ultrasonography do. The present system does not require the use of an anesthetic or a lengthy recuperative period to resume normal visual tasks. The system is fast and simple to use by the doctor and convenient for the patient. It is quantitative and less subject to observer bias and interpretation, interobserver variation or inter-test fluctuation.

DESCRIPTION OF THE DRAWINGS

The invention will be more fully understood from the following detailed description taken in conjunction with the accompanying drawings in which.

DETAILED DESCRIPTION OF THE INVENTION

Figure 1A:
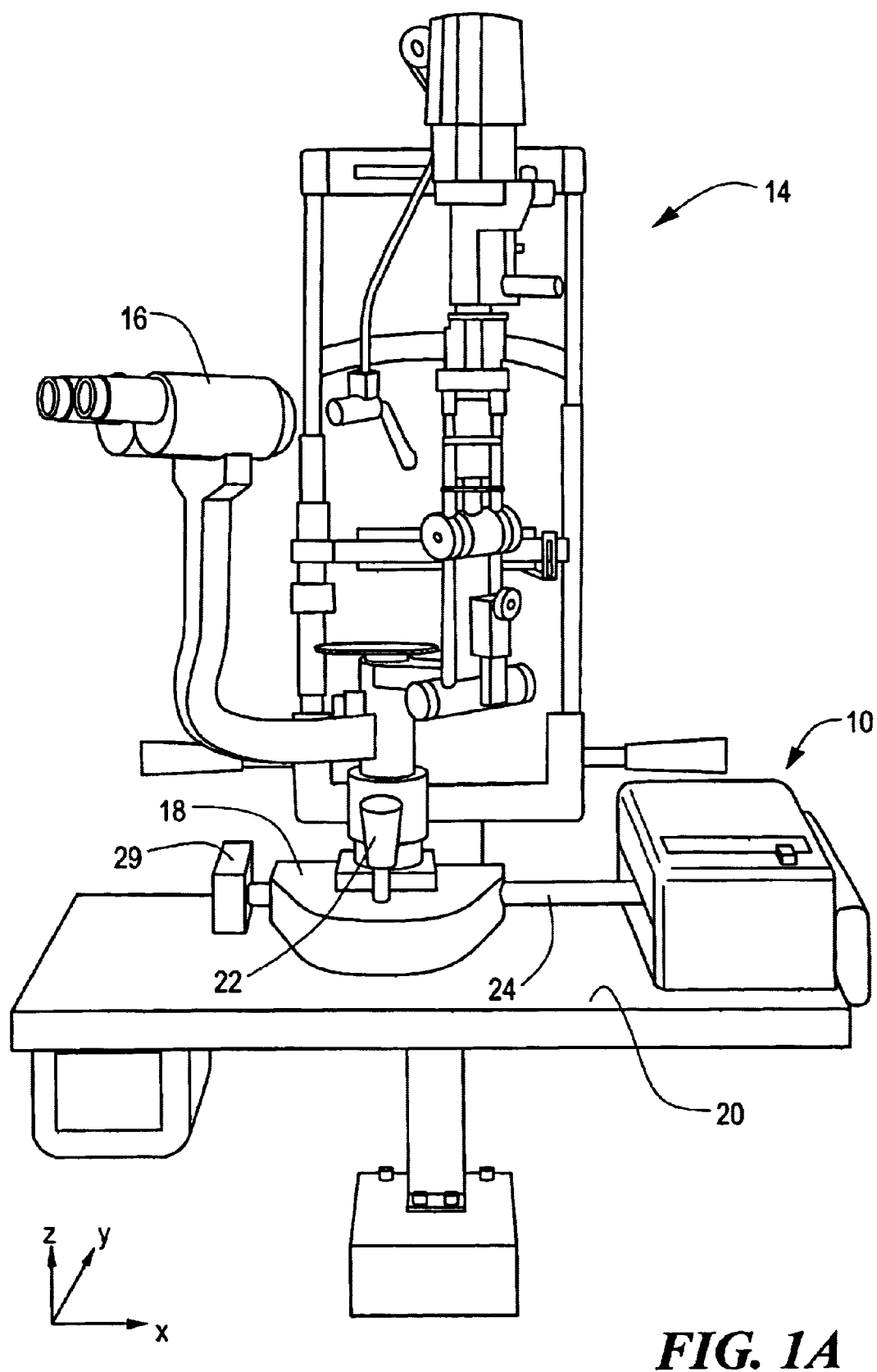
FIG. 1A is a schematic front view of an anterior chamber measurement system in conjunction with a slit lamp ophthalmology examination table according to the present invention.
Figure 1B:
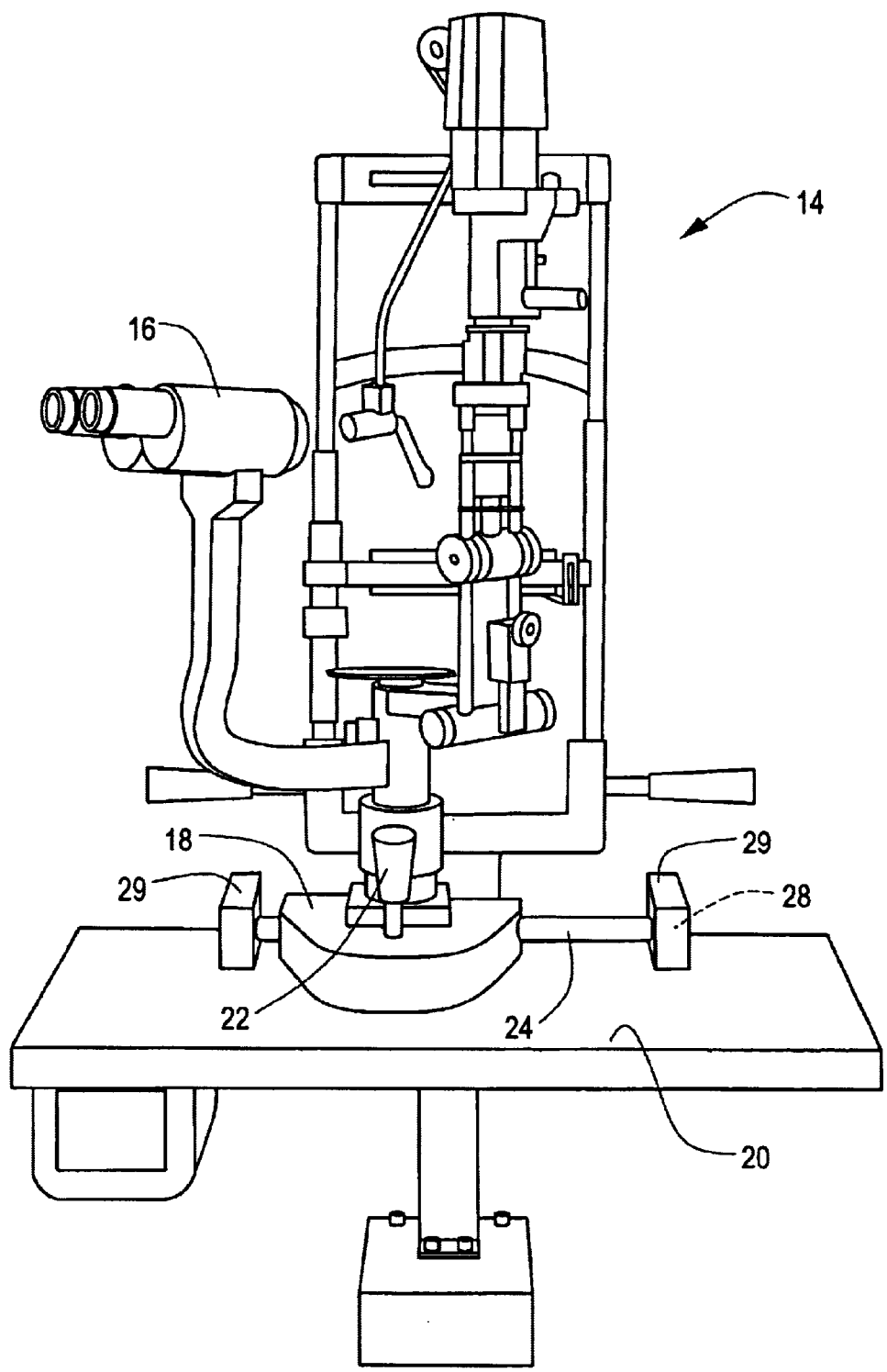
FIG. 1B is a schematic view of the slit lamp ophthalmology examination table of FIG. 1A with the anterior chamber measurement system removed.
Figure 2A:
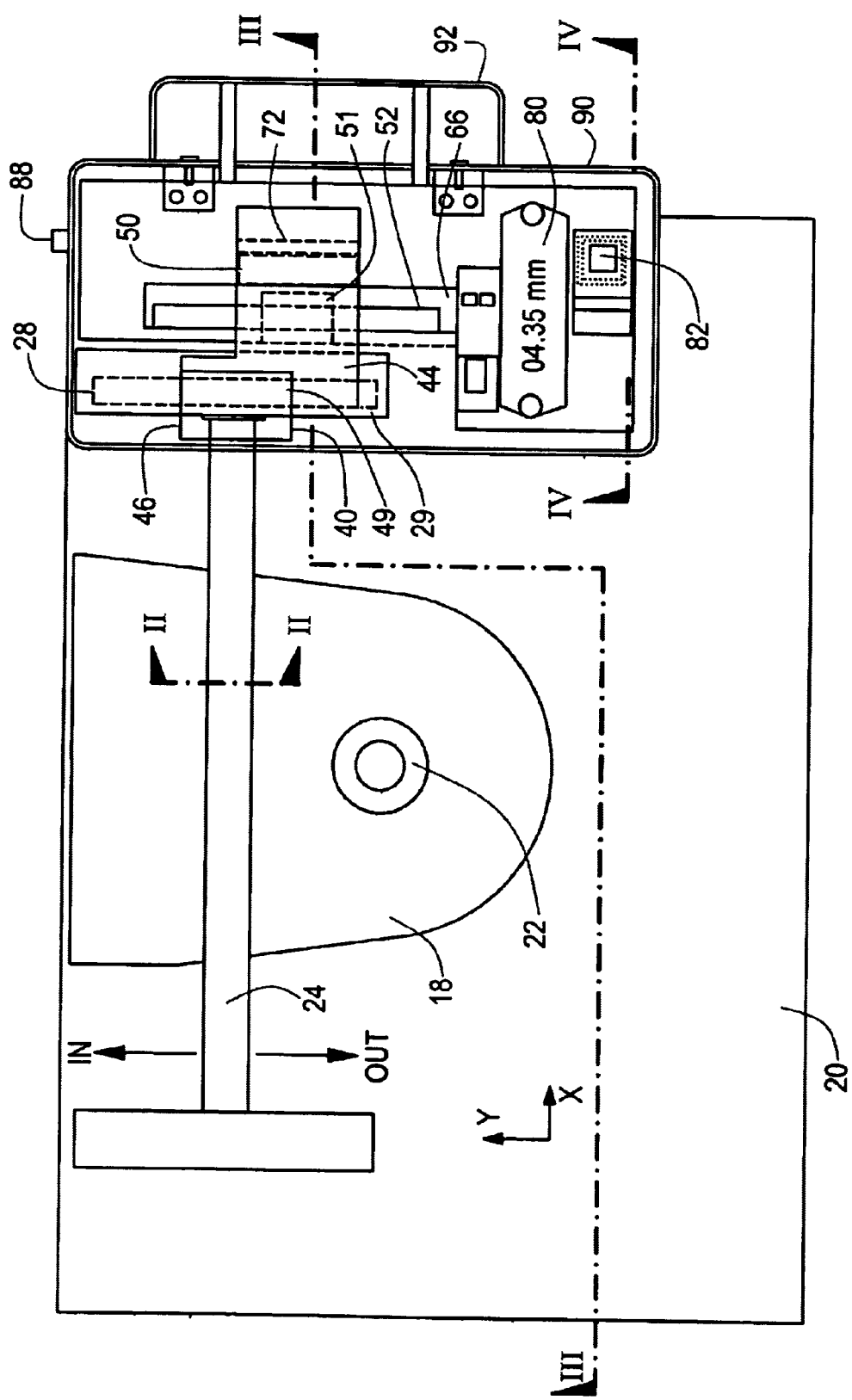
FIG. 2A is a top plan view of the measurement system and the slit lamp table of FIG. 1.
Figure 2B:
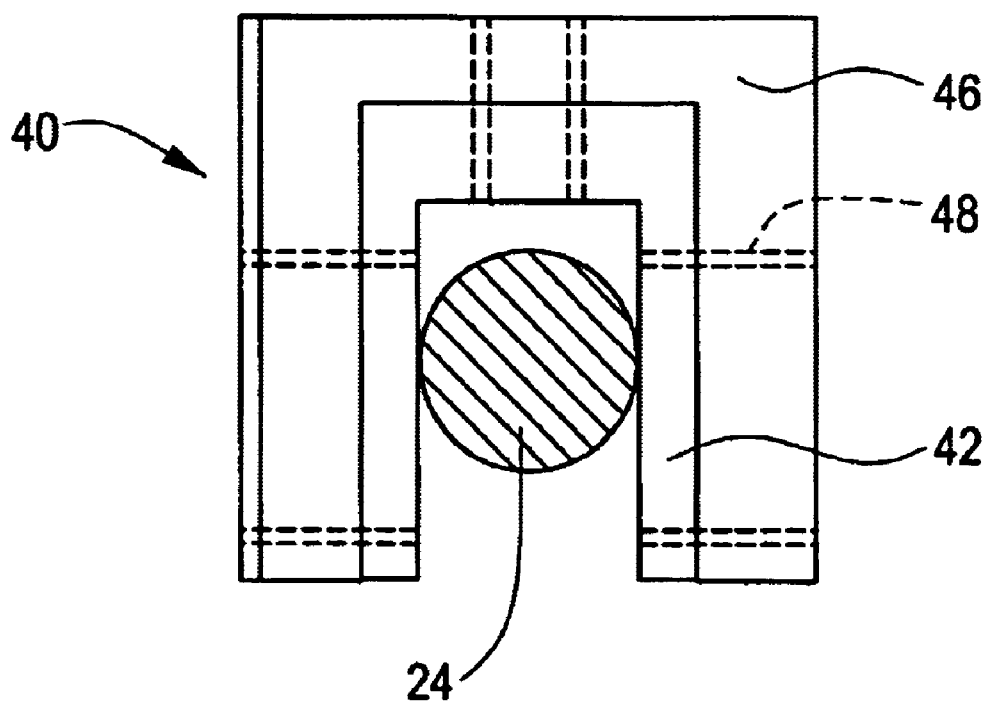
FIG. 2B is a partial cross-sectional view along line II—II of FIG. 2A.
Figures 3, 4:
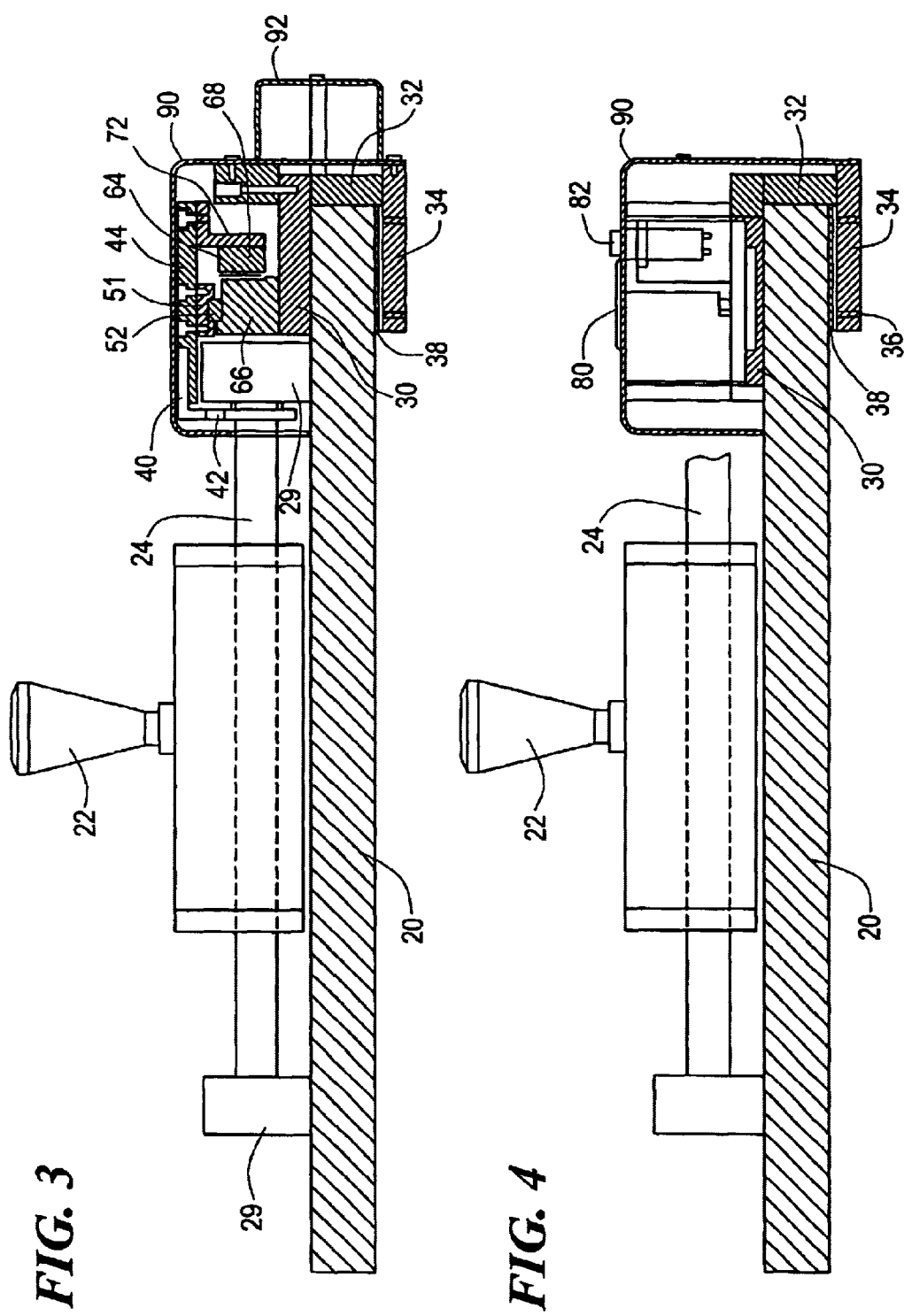
FIG. 3 is a cross-sectional view along line III—III of FIG. 2A.
FIG. 4 is a cross-sectional view along line IV—IV of FIG. 2A.
Figure 5:
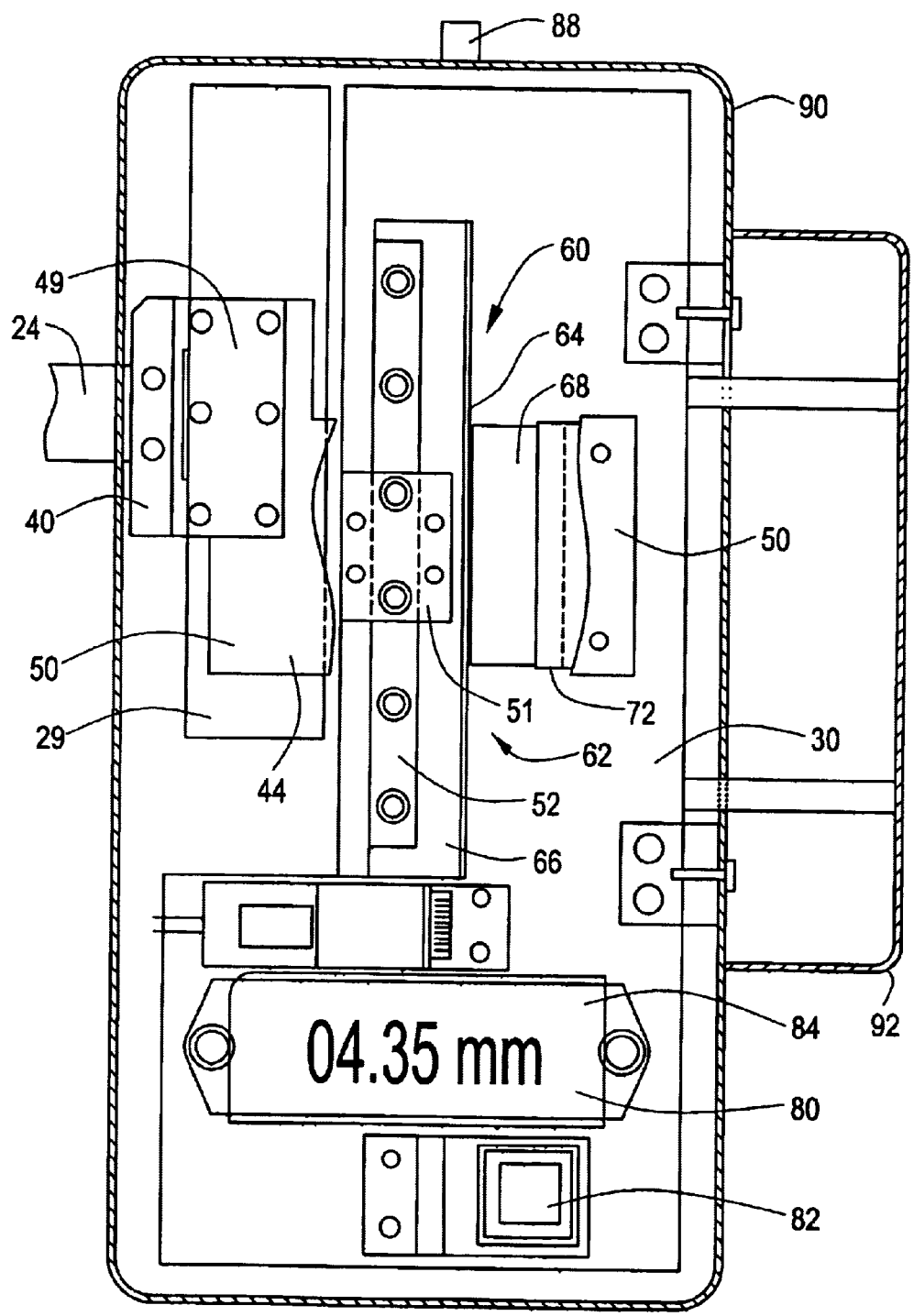
FIG. 5 is a partially cut away top plan view of the measurement system of FIG. 1A.
Figure 6:
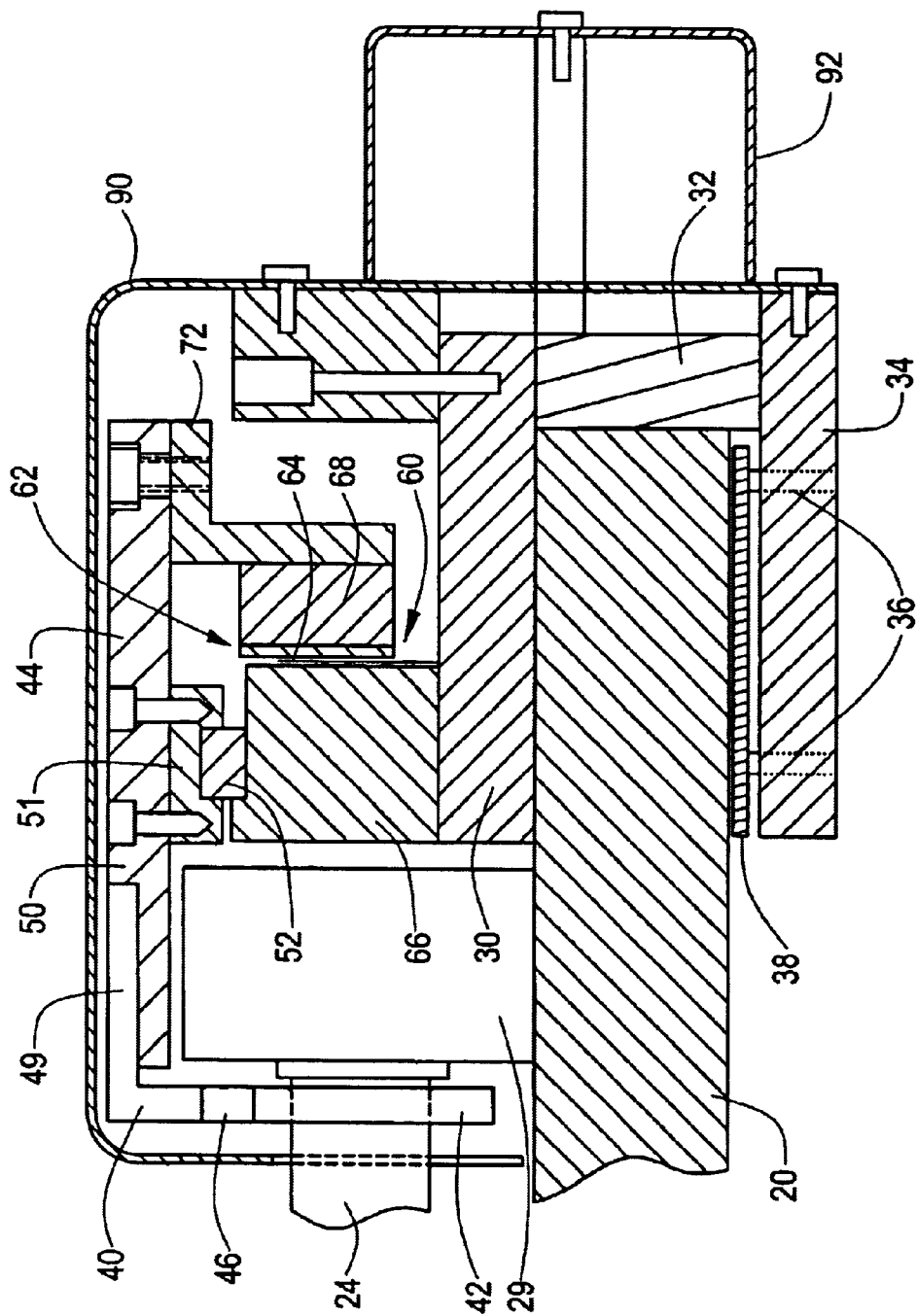
FIG. 6 is an enlarged cross-sectional view of FIG. 3.
Figure 7:
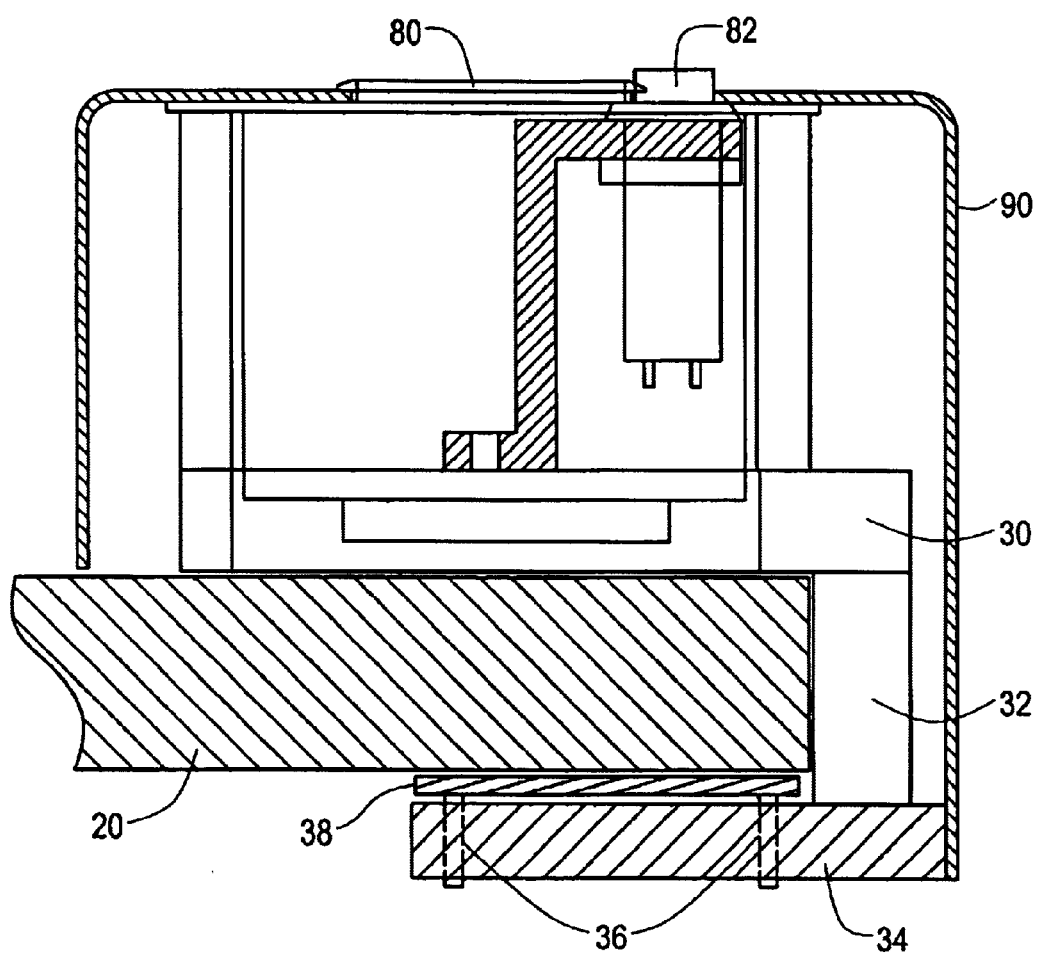
FIG. 7 is an enlarged cross-sectional view of FIG. 4.

The anterior chamber measurement system of the present invention allows a user to readily make multiple distance measurements in the anterior chamber of the eye for purposes such as the detection and diagnosis of scleric angle closure, a process that may lead to glaucoma in a more advanced state. A first embodiment of an anterior chamber measurement system 10 is shown generally in FIGS. 1A and 2A. In this embodiment, the measurement system interfaces with an existing slit lamp ophthalmology examination table 12. (See FIG. 1B.) A slip lamp 14, a device that is commonly used in eye examinations, typically includes a stereo optical microscope 16 mounted on a movable stage 18 for motion in the X and Y directions in a horizontal plane and vertically in the Z direction. The stage is typically permanently mounted on a stable table 20 or other surface and includes a joystick 22 that is movable by the user, for example, an ophthalmologist, to move the microscope. For movement in the horizontal plane, the stage includes a horizontal drive shaft 24 along which the microscope is movable in the X direction. Typically, the drive shaft is 16 or 18 mm in diameter, but the shaft is not limited to these diameters. The shaft is further mounted for movement in the Y direction along the optical axis of a patient's eye, typically over a range of 76 mm or other distances determined by the specific slit lamp. Typically, a set of rack and pinion mechanisms 28, enclosed within separate housings 29, is provided for the Y-direction motion. In the illustrated slit lamp configuration, the shaft rotates as the motion is advanced, although other slit lamp configurations are possible.

Referring to FIGS. 2A–7, the measurement system includes a base 30 that mounts securely and firmly to the slit lamp table 20 in any suitable manner and to also prevent vibrations. In the embodiment illustrated, an extension 32 of the base is provided to depend downwardly along the side of the slit lamp table and a clamp plate 34 extends beneath the table. One or more adjustable clamping elements 36, such as set screws, pass through corresponding threaded holes in the clamp plate to abut against the underside of the table. Preferably, a clamp sheet 38 is provided between the clamping elements and the underside of the table to distribute the clamping pressure from the clamping elements and to protect the underside of the table against marks from the clamping elements. Any other suitable clamping mechanism, as would be known in the art, may be provided. The clamping mechanism may be readily removable if desired, for example, if the measurement system is to be used with more than one slit lamp table. Alternatively, the measurement system may be permanently affixed to the slit lamp table in any suitable manner.

The measurement system includes an interface 40 to the slit lamp horizontal drive shaft to travel with the drive shaft in the Y direction orthogonal to the axial length of the drive shaft. The drive shaft interface includes a forked shaft pick-up 42 that fits snugly over the slit lamp drive shaft 24. The shaft pick-up 42 is mounted to a linearly translatable slide mechanism 44, discussed further below, which overlays the rack and pinion mechanism 28 in its housing 29 and yields a precise motion following the shaft 24 in the Y direction. Thus, as the microscope is moved in the Y direction along the optical axis of the patient's eye, the shaft pick-up and the slide mechanism move the same distance.

The slide mechanism 44 is coupled to a linear measurement device 60. In the preferred embodiment, the linear measurement device includes a linear encoder 62. (See FIGS. 5 and 6.) The linear encoder includes a scale 64 such as a steel tape having a suitable grating thereon fixed to a scale mount bracket 66 on the base 30. The encoder also includes an opto-electronic scanning read head 68 mounted to the slide mechanism 44 via bracket 72 for movement along the scale 64. A grating periodicity of, for example, 20 micrometers provides a typical linear resolution of less than 1 micrometer. The read head 68 is spaced suitably from the scale by a distance, for example, 0.75 mm, which can be precision set by a spacer gauge, as determined by the encoder. Suitable optical scale linear encoders with the desired resolution are commercially available.

In the embodiment illustrated, the slide mechanism 44 includes a slide yoke 46 to which the pick-up fork 42 is mounted. (See FIG. 2B.) The pick-up fork is composed of a low friction material. An adjustment mechanism 48, such as one or more set screws, may be provided to set a desired clamping pressure of the pick-up on the drive shaft 24, so that the pick-up moves readily with the shaft without binding or backlash. The slide yoke is fastened via a bracket 49 to a slide plate 50. (See FIGS. 2A, 5, and 6.) A carriage 51 extends from the slide plate and rides on a rail 52, which is fixed to the scale mount bracket 66. The read head 68 is mounted to a mounting bracket 72 that depends from the slide plate 50 so that the read head faces the scale. Thus, as the drive shaft 24 of the microscope is moved in the Y direction, this motion is translated via the shaft pick-up 42 and the slide mechanism 44 to the read head 68, which in turn passes over the grating on the scale 64, thereby reading a determination of the distance traveled by the microscope in the Y direction.

Figure 8:
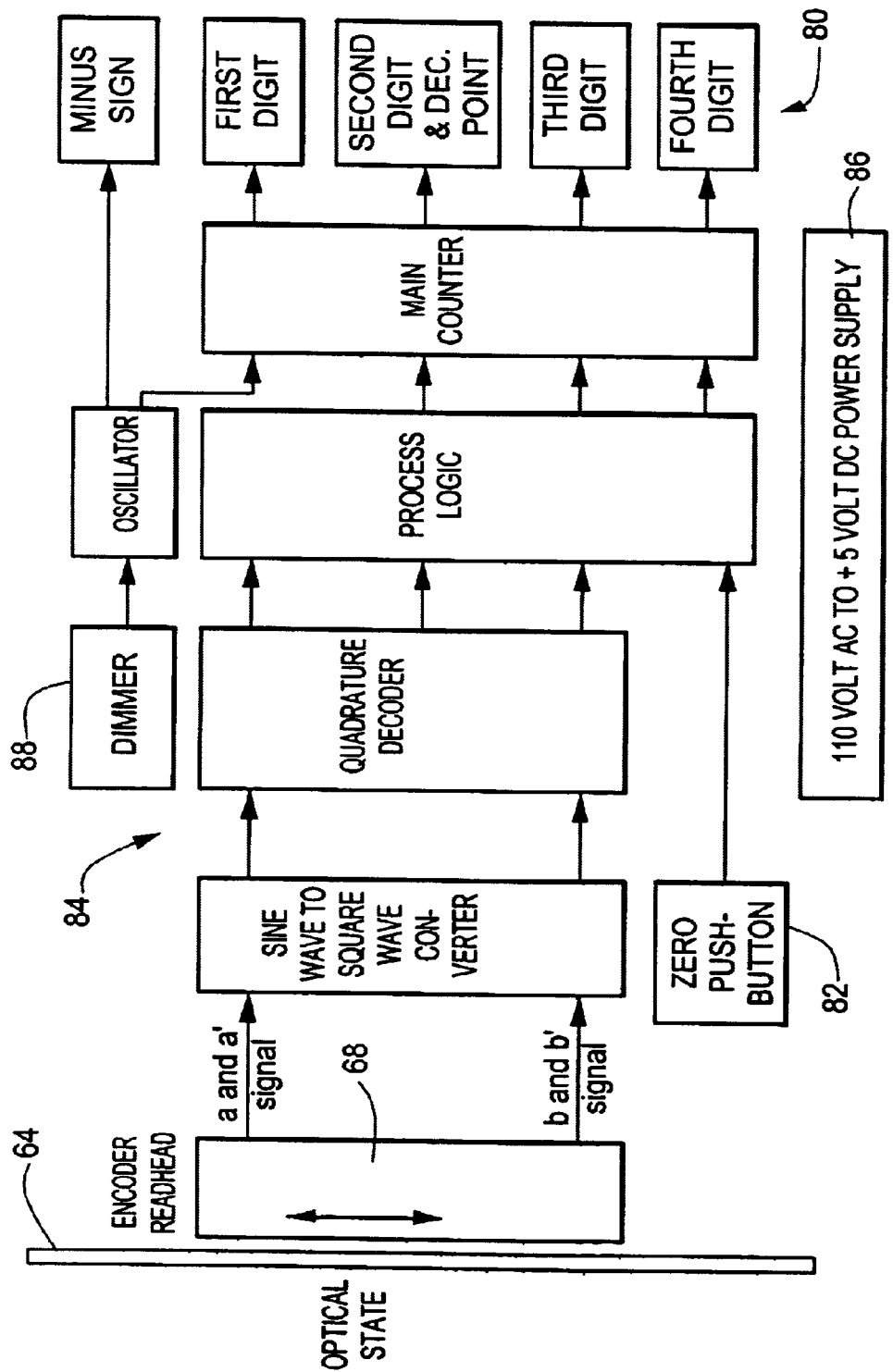
FIG. 8 is a schematic circuit diagram of the measurement system of FIG. 1A.

The read head 68 is in electronic communication with suitable circuitry 84 that is operative to translate quadrature signals from the read head to a suitable display 80, such as an LED display, to provide distances traveled to a desired accuracy. For example, a three-digit display may be used to provide 100 micrometer accuracy or a four-digit display to provide 10 micrometer accuracy. The display may be set to zero at any time by pushing a suitable button 82 in communication with the display. FIG. 8 illustrates a schematic of suitable quadrature and LED display circuitry.

Figure 9:
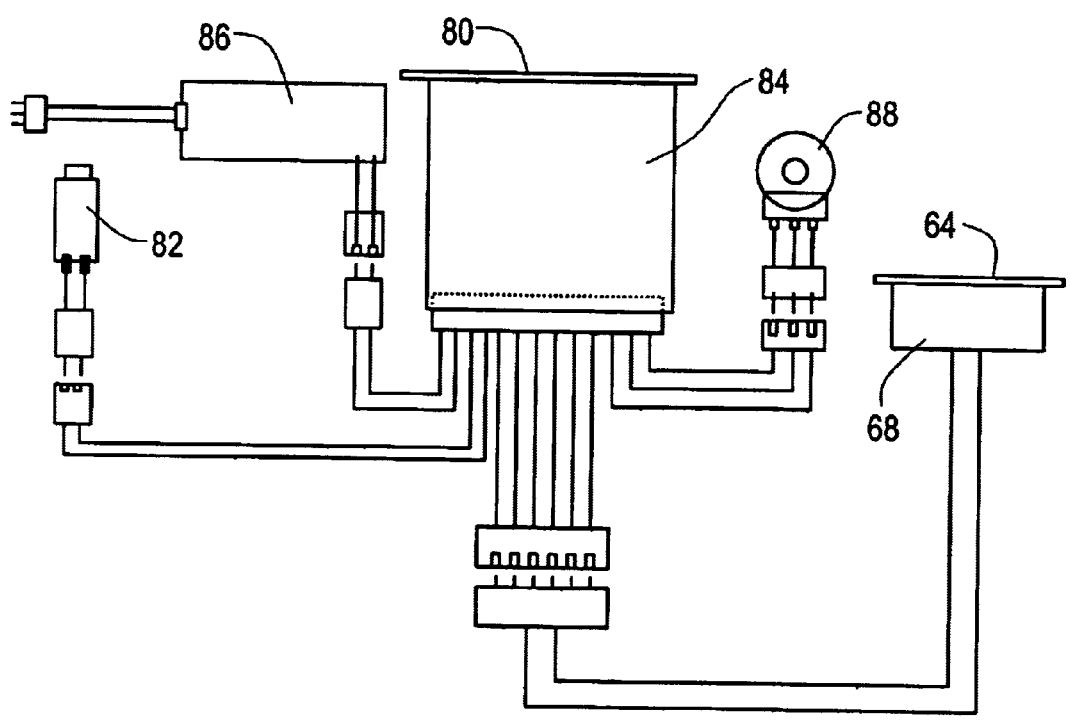
FIG. 9 is a schematic wiring diagram of the measurement system of FIG. 1A.
Figure 10:
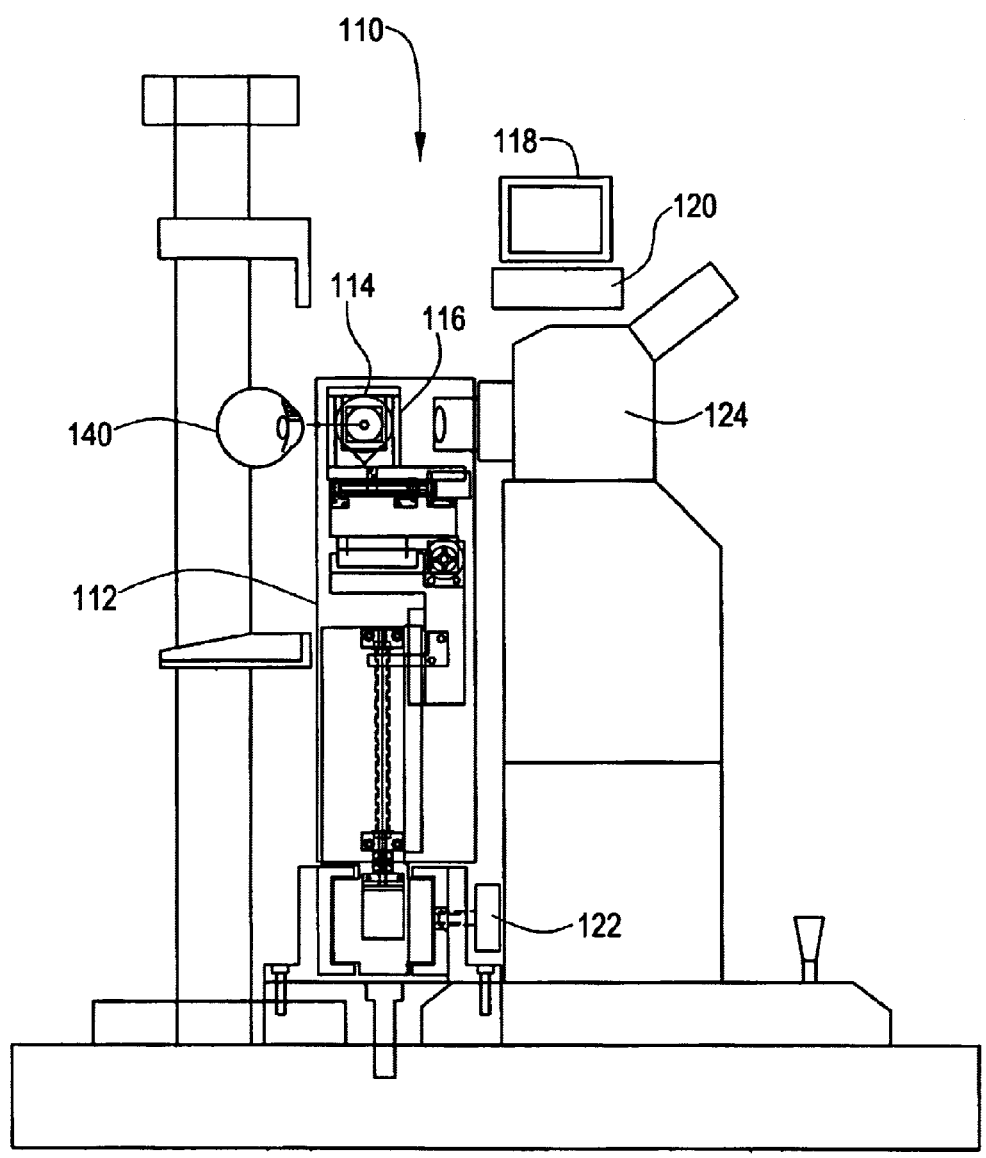
FIG. 10 is a side view of a further embodiment of a measurement system according to the present invention.

The measurement system also includes a power supply 86, such as a 5 volt power supply, that plugs into a conventional wall outlet. The power supply provides power to the read head 68, the LED display 80 and the electronics 84. An LED dimmer potentiometer 88 is provided to adjust the brightness of the LED display. Push button 82 sets all LED readout digits to zero at any position of the shaft 24. The various components are in electrical communication via suitable wiring and connectors, as indicated schematically in FIG. 9.

The measurement system is covered with a suitable cover 90 to protect the components from dust and dirt and provide a pleasing appearance. In the embodiment illustrated, a separate cover 92 is provided for the power supply and some of the electronics, although it will be appreciated that any other suitable arrangement of the components within any suitable housing or covering may be provided.

The regions of interest within the eye for measurements, for example, to detect and diagnose scleric angle closure, extend over the full surface of the ring formed by the iris and the forward space between it and the inside surface of the cornea. The distance between cornea and iris in a healthy person ranges from about 2 mm on the edge of the eye to about 3 mm near the center of the eye and varies somewhat with each individual. Knowledge of these distances is most valuable to the diagnosis if these distances are measured parallel to the optical axis of the eye and in nearly all areas of the iris. The accuracy of measurements needed for good diagnosis should be made to tolerances of about 0.1 mm (100 micrometers) and preferably 0.01 mm (10 micrometers). Consolidated data of these measurement results allow the plotting of the shape of the scleric angle, which significantly aids diagnosis and the decision process of post diagnostic medical treatment. With periodic measurements, the history of a patient's scleric angle closure can be traced over time. Documentation of its progress allows appropriate and timely treatment.

To make a distance measurement between cornea and iris, the user first finds the location in the eye to be measured using the stereo microscope and the joystick control of the slit lamp. Next, the user finds the best focus with the stereo microscope in the plane of the cornea, then pushes the zero button, which causes all the numbers on the display to show zero. The user next moves the microscope to focus on the surface of the iris. The distance traveled in the Y direction is detected by the measurement system and displayed to a desired precision in millimeters or other desired units as the distance from cornea to iris. This distance and location within the eye are recorded by the user on a measurement data sheet or automatically. The user repeats this measurement procedure on every other location within the eye required for diagnosis.

In a further embodiment, if it were desired to automatically record the data, the system may be provided with an appropriate connection, such as an RS 232 serial bus interface, to a peripheral device such as a printer. A print command button may be included on the measurement system to cause the system to print out the recorded values. The measurement system may also interface with an appropriate computer or include an appropriate microprocessor and memory to provide automated graphing or charting capabilities, statistical analysis of the measurements, and past patient history of anterior chamber measurements. In a further aspect, measurement scales may be included that interface with the X and Z motion stages of the slit lamp to manually move the slit lamp to predictable eye locations, where measurements in the Y-direction are made as described above.

In a further embodiment of the present invention, illustrated in FIGS. 10–14, a measurement system 110 includes a three-axis stage assembly 112 supporting an optical microscope assembly 114 that interfaces with a digital CCD camera 116 and television monitor 118 under the control of a suitably programmed controller or computer 120. Television frames of the eye are analyzed on the fly to store in memory unique signal signatures associated with in-focus features and their measured location between the cornea and the iris. The system includes an engagement mechanism 122 to engage and disengage with an existing slit lamp microscope 124. In an alternative, the system may be configured as a stand-alone measurement system used solely for making anterior chamber distance measurements.

Figure 11:
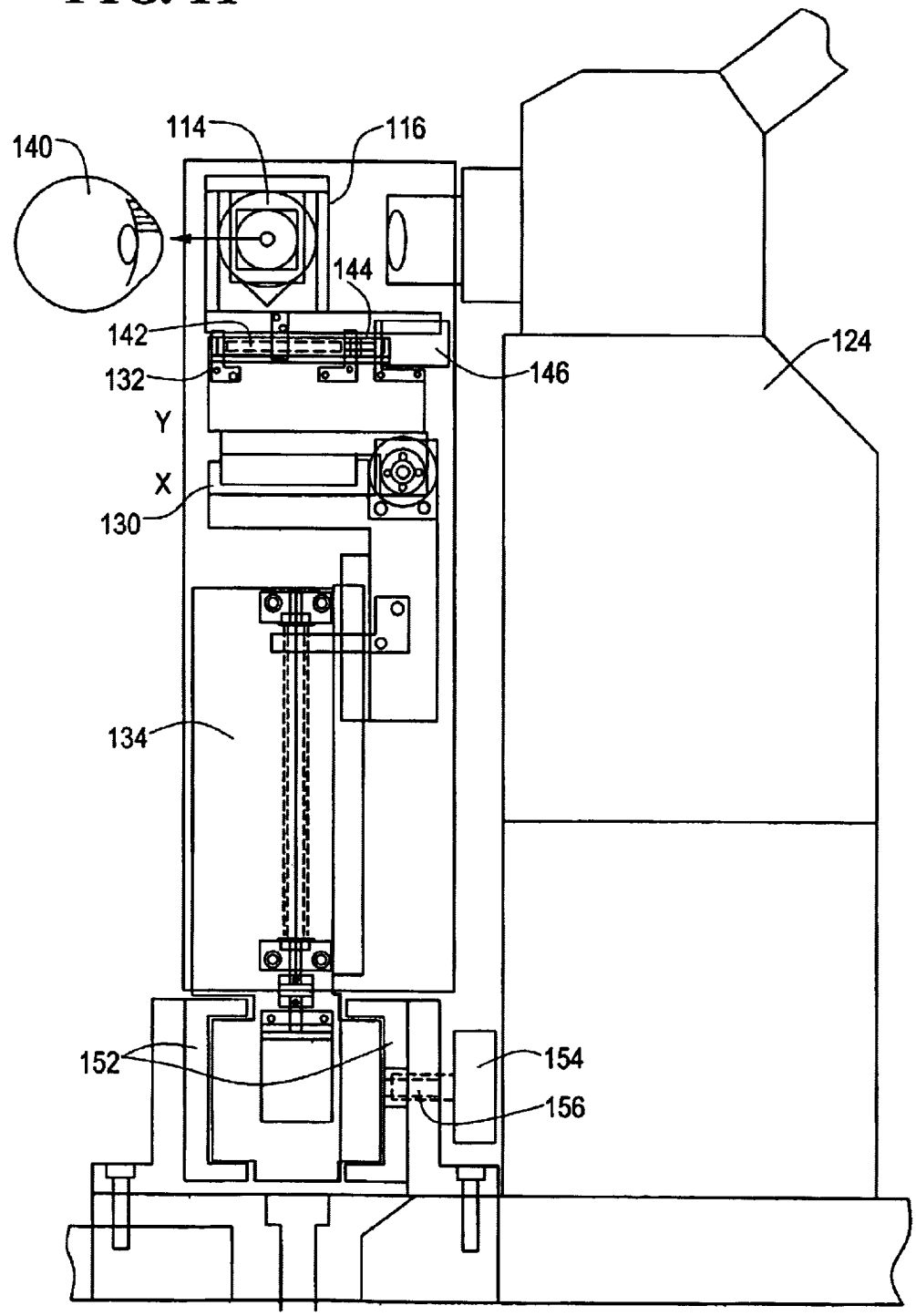
FIG. 11 is an enlarged view of the measurement system of FIG. 10.
Figure 13:
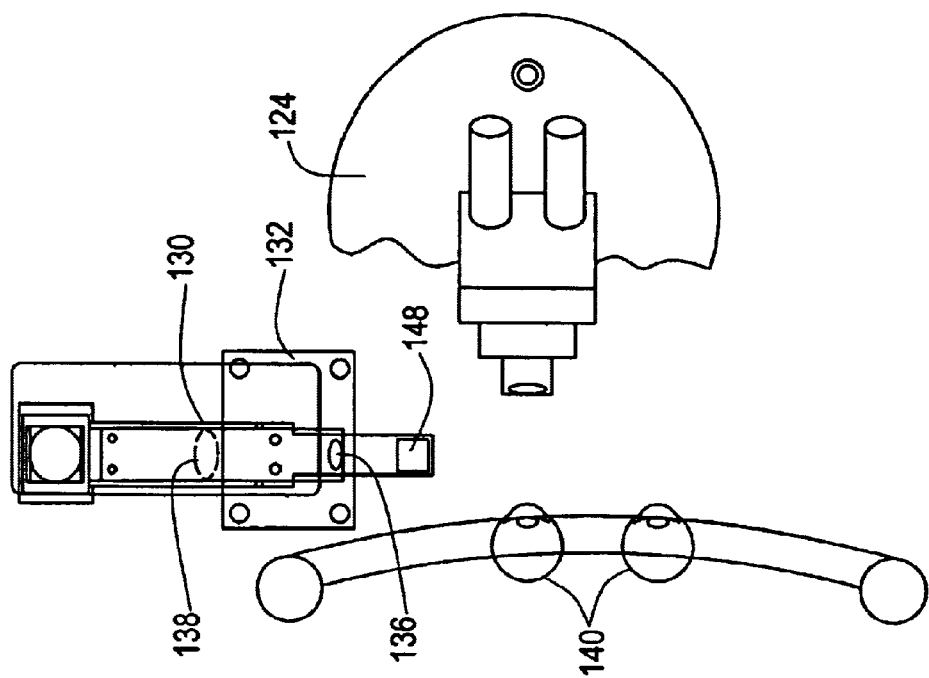
FIG. 13 is a partial top view of the measurement system of FIG. 10 in a disengaged position.

Referring more particularly to FIG. 11, the measurement system includes three motorized precision stages that move the optical axis of the optical microscope assembly in the X, Y and Z direction in front of the eye 140, under control of the computer 120. The microscope assembly 114 is mounted on top of the three motor controlled stage axes that are stacked on top of each other. The X-axis stage 130 is used to move the optical axis to either eye and to the precise area in the eye where a measurement is to be made. The Y-axis stage 132 is used to move the focal plane of the microscope assembly to the cornea and to the iris, or any other elements in the anterior chamber, where distance measurements are to be made. The Z-axis stage 134 is used to move the optical axis up and down to predetermined vertical positions in the eye where measurements are to be made.

The optical microscope assembly 114 works in conjunction with the digital camera 116 such that images of the eye are observable on the television monitor. In this embodiment, the slit lamp's stereo microscope with eyepiece is not needed. The three-axis stage assembly, located below the microscope, supports and moves the microscope assembly to reach all parts of both eyes where measurements are needed.

The optical microscope 114 is selected to have a magnification factor sufficient to discern features within the eye and to provide a field of view sufficient to locate a desired region of the eye. In the present embodiment, the microscope assembly includes an objective lens 136 and a tube lens 138 to focus the image onto the camera 116. Suitable microscopes, cameras, and television monitors are commercially available. An illumination light source may also be part of the microscope assembly. Alternatively, a slit lamp illumination may be used, such as when the system is part of a conventional slit lamp eye examination table 124. The microscope assembly 114 is positioned to look directly into the patient's eye 140 and focus on the cornea's internal surface and subsequently on the iris. This optical assembly is mounted on top of the three-axis motor driven and computer controlled motion stage assembly 112 to manipulate the optics to aim at important areas of the eye, where measurements are to be made, as directed by the user.

The Y-axis motor stage 132 moves the optics toward and away from the eye over a controlled distance of about 40 mm along the optical axis of a patient's eye to conduct the measurements. The Y-axis motion stage is made up of a slide mechanism 142, for example, a precision linear ball slide, that moves over a suitable length, for example, 40 mm, and to which the optical assembly 114 is mounted. For example, a precision screw/nut combination 144 with a pitch of 5 mm may be provided to move the slide (and the optics with it) back and forth under the force of a step motor 146. There is no need for optical scales, since the steps fed to the motor are sufficiently accurate and are counted by the driving electronics to make accurate distance movements. The motor motions are directed by suitable software in the microcomputer 120. The motions of the Y-axis stage may be controlled manually by pushbuttons on a control pad, by a joystick, or automatically by the microcomputer.

The X-axis motion stage 130 in its implementation is similar to the Y-motion stage, except it points in the X-direction and moves the optics over a longer distance to reach all areas of both of the patient's eyes. The range of motion is typically up to 150 mm. This motion may be manually controllable by joystick or pushbutton as well as automatically by computer.

The Z-axis motion stage 134 is similar to the others, except it is arranged to move all items above it up and down to place the optical axis anywhere in the vertical direction of the eye. The extent of motion is typically 80 mm to accommodate smaller and larger patients' heads on the same headrests. This motion may be manually controllable as well as automatically by computer.

Figure 12:
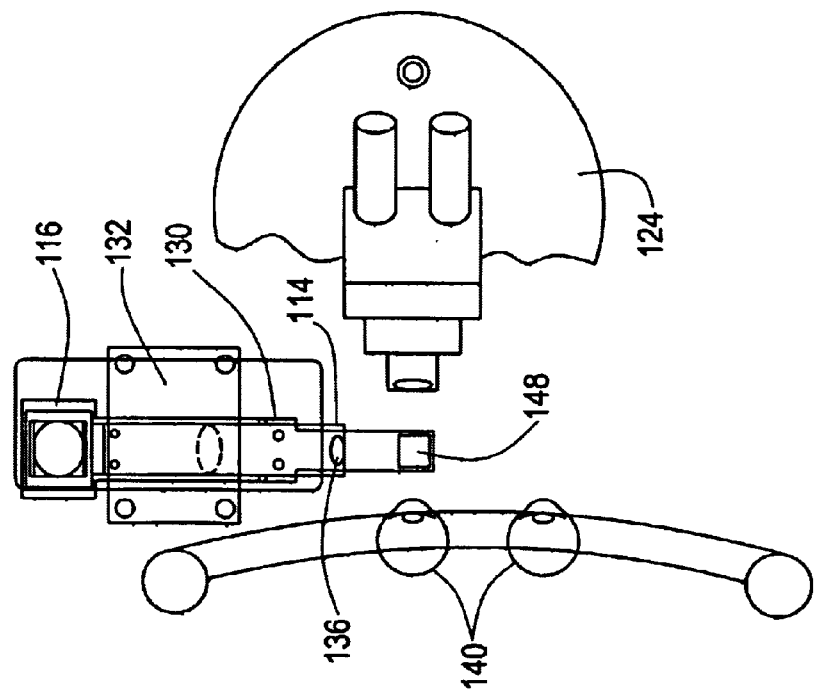
FIG. 12 is a partial top view of the measurement system of FIG. 10 in an engaged position.

The engagement mechanism 122 for the measurement system is installable on conventional slit lamp examination tables 124 so that the system can operate in conjunction with an existing slit lamp table. Because the space in front of the patient is occupied by the slit lamp and stereo microscope, the system is arranged not in front of the patient, but to the patient's side, typically, the right side, with the optical axis aligned in the X-direction. A right angle mirror 148 is placed in front of the patient so that the optical axis again in line with the eye. This mirror and all parts of the system stack are moveable to the side to disengage the measurement system and to allow conventional access with the stereo microscope and the slit lamp to the eye. The engagement mechanism 122 may, for example, be a set of precision ball slides or tracks 152 and a handle 154 that the user operates to push the system from the engage stop to the disengage stop, or vice versa. A suitable locking mechanism 156, such as a screw, may be provided to hold the system solidly in either position. FIG. 12 illustrates the measurement system in the engaged position and FIG. 13 in the disengaged position.

Figure 14:
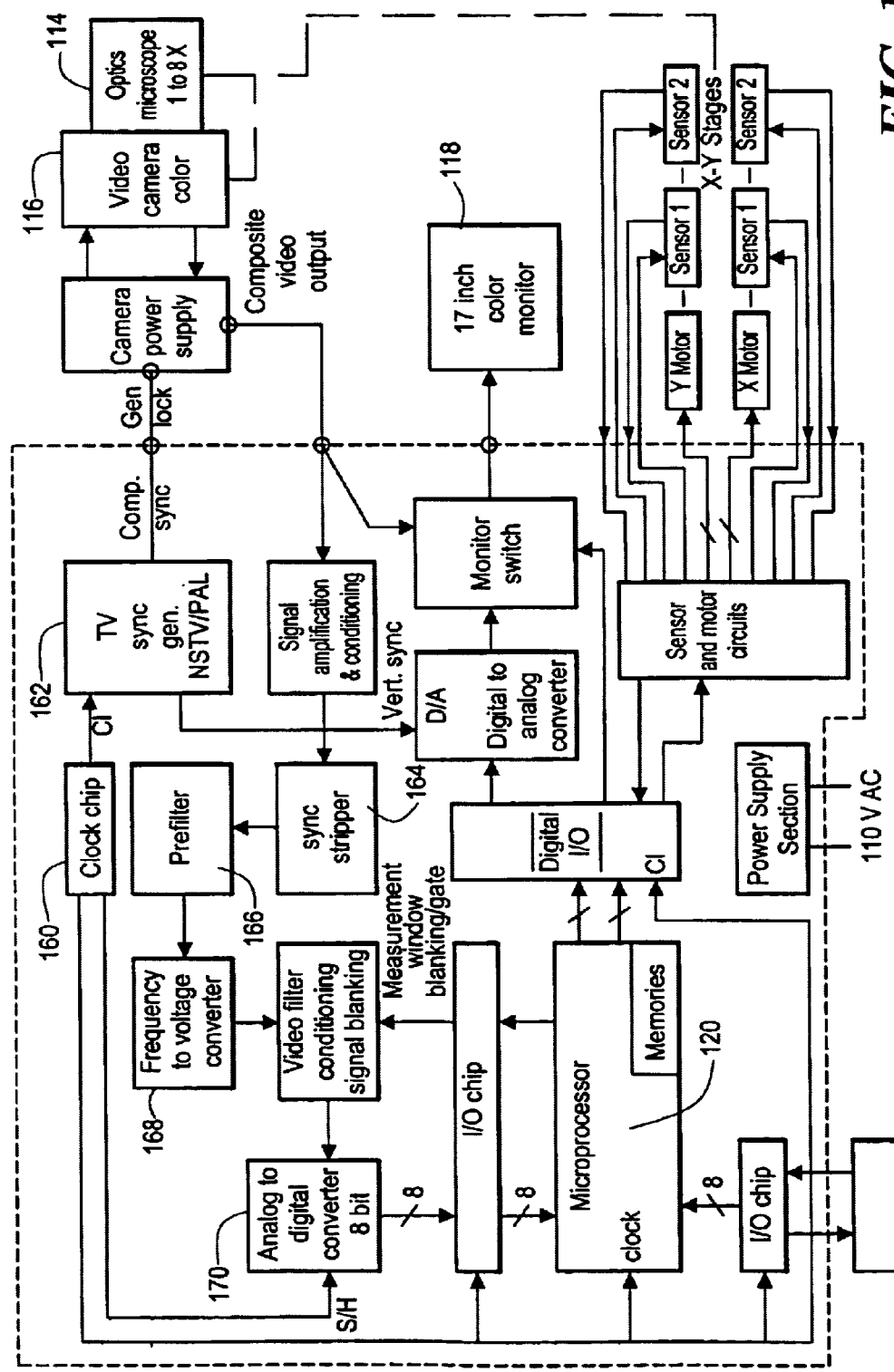
FIG. 14 is a schematic block diagram of the electronic system of the measurement system of FIG. 10.

The electronics and its subsystems are depicted in the block diagram of FIG. 14. The camera and monitor electronics are conventional commercial components. The digital CCD color camera (NSTV or PAL, the US and European television standards) is synchronized to a system clock 160 via a television sync chip 162 that produces the vertical and the horizontal sync signal to the camera's "Genlock." The microcomputer's clock is derived from the same clock source and all timing components are thus synchronized with each other, namely the camera, microcomputer, the step motors and the television frames. This arrangement allows the timing of advances of the measurement optics with the Y-axis motion stage 132 in step with the 30 frames per second of the color TV system.

With each step advance of the Y-motion stage 132, one television frame is generated at 1/30 of a second, with its video signal distribution of that particular depth position in the eye. The composite video signal is fed to the monitor for display and also to the analysis electronics. In the electronics hardware, the sync portion of the signal is stripped off by sync stripper 164 and the video signal remains. It is filtered by pre-filter 166 to contain certain bandwidths only and is then fed into a frequency to voltage converter chip 168. The output yields essentially relatively higher voltages in areas of the image where relatively more higher frequency content is found. Higher frequency content in an image represents areas that are in focus or where relatively more details are imaged. Conversely, lower voltages are generated in areas that are out of focus or where no image features are present. These analog voltages are converted to digital signals by A/D converter 170 to make them compatible with the microcomputer.

With this arrangement, the three-dimensional location of in-focus conditions in the eye can be determined, namely in the vertical, horizontal and depth directions. The vertical and horizontal planes are measured from the television frame, while the depth position of each television frame generated is determined by the optical system's depth position as it is moved with the Y-motion stage. As a result, three sets of data are available that must be further processed in the microcomputer. The mapping of the eye from the cornea to the iris is thus a series of television frames (known as tomography), each taken and analyzed on the fly after the Y-axis motion stage has made one small step forward toward the iris. At that moment, the stage is held in a fixed position for a short time equivalent to the television frame being taken, for example, 33.3 milli-seconds minus the vertical retrace time of 5 milli-seconds, or 28 milli-seconds. During the retrace portion of the television's frame, the Y-axis motion stage advances by one motor step. In this manner, many frames are obtained from the cornea to the iris. The size of the small steps defines the depth resolution of the frame stack as well as the amount of time it will take to finish a measurement run. For instance, if the frame advance rate is operated at a frame spacing of 50 micrometers, which is a suitable depth measurement, then the motor step must advance at the same rate, namely 50 micrometers per motor step. Since the two-phase step motor employed on the Y-axis motion stage makes 200 steps per advance screw revolution, and each step is to be 50 micrometers, the screw pitch must be 50×200, or 5000 micrometers, or 5 mm. This is the distance needed to move at a rate of 30 steps/second (or 30 television frames per second) for 200 frames. The depth run will therefore take 200/30=6.7 seconds. If more frames were desired at a higher depth resolution, then it would take proportionally longer to make a depth measurement run. If more depth resolution is desired, the screw requires a smaller pitch and a depth run would take more time. This would also require steadiness of the patient for a longer time.

Various optimization strategies may be employed to reduce the time of a depth run. For example, a strategy that avoids taking frames in the aqueous space in the eye between cornea and iris can be employed. The aqueous space can be learned for each patient and can be skipped, as no analysis would be required in this space. Across that space, the motor can be run quickly and the time can be reduced substantially. Other schemes may be employed for further optimization, as may be known in the art.

The television monitor image typically depicts the outline of the iris plus some rim space. Before the run is started, the user determines the field of view of the area of the eye to be investigated and selects the zoom setting in the optics to cover that area of interest. This area may be the full iris or any fraction thereof, for example, 1/10 of the iris.

After the desired size is set up, the user focuses manually, via pushbutton or joystick control, on the inside surface of the cornea in the center of the image. Since the cornea is curved, the user focuses on its most forward part as seen in the image. Imperfections in the cornea can help in focusing. The measurement start button is pushed and the system proceeds to measure the distance to the iris.

Figure 15:
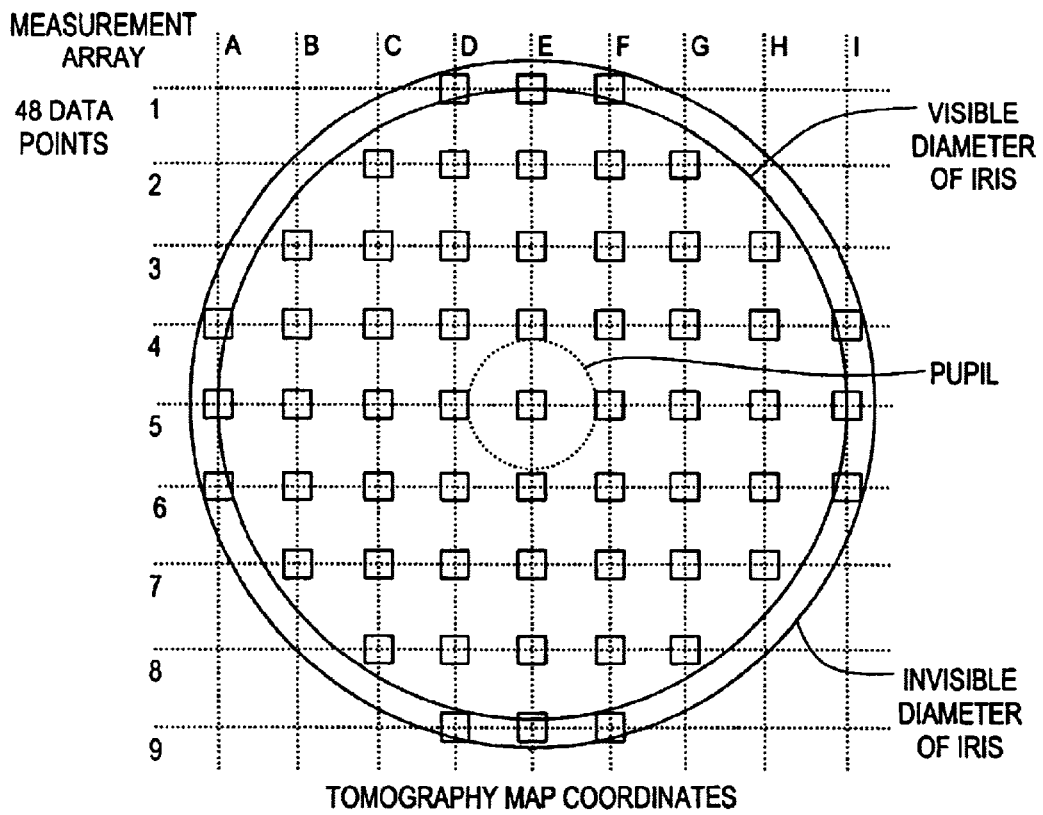
FIG. 15 is a graphical display of tomography coordinates used in mapping an eye according to the present invention.
Figure 16:
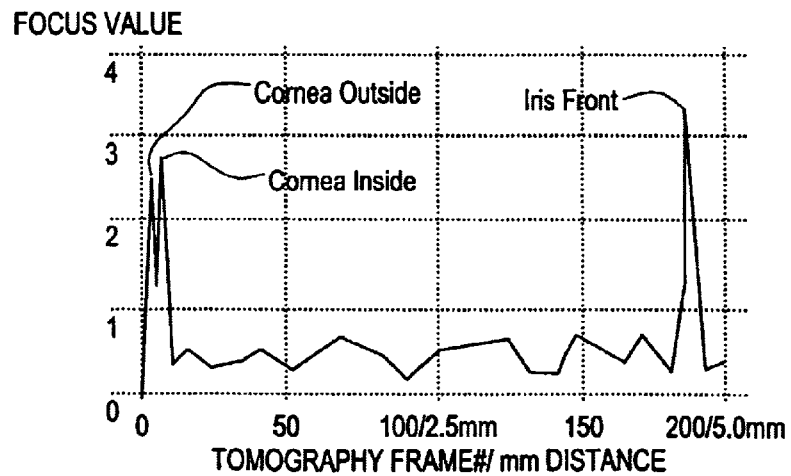
FIG. 16 is a graphical display of focus values in one area of an eye according to the present invention.
Figure 17:
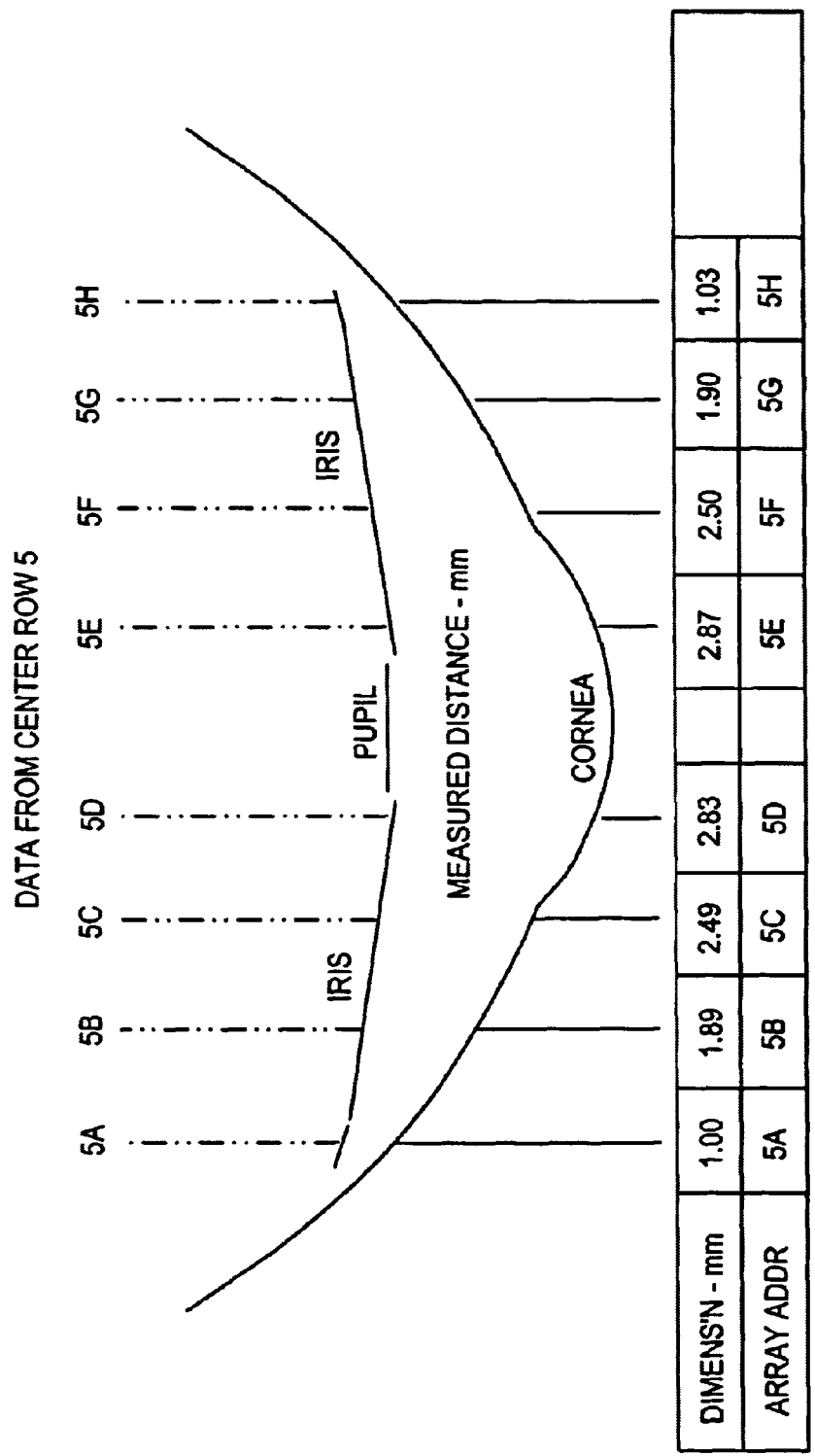
FIG. 17 is a graphical display of a cross-sectional top view of an eye illustrating distances measured between cornea and iris according to the present invention.

With the tomography scan of the eye covering the total iris and the hidden iris outside the visible area, the specific area scan option may be selected by the user on the keypad or on the television screen. In this mode, the iris area is divided into a suitable number of areas arranged in an array of small squares, as depicted in FIG. 15. Each of these areas is gated on (enabled to pass the video signal), when the television frame scan is active in each of the areas. For each area, the frequency component signal is fed to computer memory, associated with the frame number of the depth scan. This data is correlated in the microcomputer after the scan is completed and is listed as numeric values associated with in-focus points and their depth positions. From this data, the scleric angle can be calculated and, if desired, compared to values previous determined for a patient to learn whether the closure has become more or less severe. Such calculations and comparisons may be performed either by the microcomputer or by the user. FIG. 16 illustrates an example of focus values in one area of the eye. Similarly, the data can also be presented in graphic form as a top view (FIG. 17) and/or side view of the eye, showing the real curvature of the eye cornea and the iris behind it to judge the associated scleric angle. Historic plots gleaned over the patient's history can be overlaid, optionally in different colors, to discern worsening or improvement of the condition over time.

Instead of using an "on the fly" image analysis, as described above, the system may also employ a more advanced computer with a television frame grabber and more image memory capacity. In this case, the depth scan is taken as above, and all the data of each tomography image is stored pixel by pixel in computer memory. Software directed analysis is done after the scan is completed. The modes of the analysis may be more involved with true signal processing of data out of memory, and history comparisons with plotting programs may be employed that give high reliability data. Software for such analysis can be adapted from software used in advanced medical imaging tools.

The primary medical application of the present anterior chamber measurement system is the measurement of the anterior chamber depth in any of its segments and in any of the desired distances from the pupillary border to the anterior chamber angle. This measurement is useful in the diagnosis and treatment of narrow angle glaucoma and in screening patients for angular abnormalities, such as impending angle closure. This measurement is useful in recording pre-operative and post-operative anterior chamber depths prior to and subsequent to a peripheral iridotomy or iridectomy and to monitor patients identified to be at risk for developing angle closure glaucoma, but who have not been treated with iridectomies. The system is useful in the monitoring of open angle glaucoma patients to determine any narrow angle component. The system may be used to quantitate changes in the anterior chamber depth following treatments such as an iridectomy, gonioplasty, or goniosynechialysis.

The system is also useful in phacointraocular lens implant surgery, a rapidly growing phase of ophthalmology. In such surgery, it is important to calibrate the anterior chamber depth to ascertain implant feasibility for a particular patient. The system is also beneficial for measuring any segment that has a suspicious narrowing that may indicate a ciliary body tumor that might indicate melanoma. The system is also helpful on a daily basis in assisting the ophthalmic technician's determination of the safety factor in mydriatic installations, as the use of a mydriatic in a narrow angle eye could theoretically precipitate an ocular crisis. The system is an adjunct to darkroom provocative glaucoma tests. The system may be used to establish the existence and extent of pathologic conditions such as angle recession.

Other variations and embodiments of the present measurement system are contemplated. For example, infrared and/or ultraviolet illumination sources may be employed. Additionally, distances may be quantified using non-imaging beam optics. For example, collimated, divergent, or convergent single or multiple beams can be detected by reflection or scattering from various eye surfaces to provide quantitative distance measurements.

Ultrasonic beams can produce readily sensed reflections from the various outer and inner surfaces of the eye. Such beams may be directed perpendicularly to the corneal surface and return reflections collected by a combined or separated detector in a timed return mode calibrated into distances. Depending upon the frequency of the ultrasonic beam, a coupling medium placed between the source and the corneal surface of the eye may or may not be required. Additionally, such beams may be directed at the eye at an angle to the corneal surface and the structure surface reflections recorded with a detector or detector array placed in a position to pick up the angularly reflected return beam. Angular directions may assume various three dimensional directions or azimuths with respect to the eye surfaces. The principles of trigonometry or solid geometry can be employed to calculate, list, or display the quantified inter-surface distances.

Alternatively, wavelengths in the visible or non-visible spectrum may be employed in such reflective non-imaging modes as with the imaging modes. Either laser or non-coherent beams may be employed.

The distances between various eye membranes or structures measured as a function of position within the eye by the above methods can be listed in tables or utilized to construct two or three-dimensional maps of the measured distances.

The invention is not to be limited by what has been particularly shown and described, except as indicated by the appended claims.

What is claimed is:

1. A measurement system for measuring distances in an anterior chamber of an eye in conjunction with a slit lamp ophthalmologic microscope assembly mounted on a slit lamp examination table, the measurement system comprising:
   a linearly movable interface assembly operative to pick up motions of the microscope assembly in a direction along an optical axis of the eye; and
   a linear measurement assembly coupled to the interface assembly and operative to determine a distance traveled by the interface assembly.

2. The measurement system of claim 1, wherein the interface assembly comprises a base fixable to the slit lamp examination table.

3. The measurement system of claim 1, wherein the base is removably fixable to the slit lamp examination table.

4. The measurement system of claim 1, wherein the base includes a clamping assembly configured to clamp to the slit lamp examination table.

5. The measurement system of claim 1, wherein the interface assembly is fixed to the slit lamp examination table.

6. The measurement system of claim 1, wherein the linearly movable interface assembly comprises a member matable with a drive shaft of the microscope assembly to travel with the drive shaft along the optical axis of the eye.

7. The measurement system of claim 6, wherein the matable member comprises a yoke member configured to fit over a portion of the drive shaft.

8. The measurement system of claim 7, wherein:
   the interface assembly includes a base and a slide mechanism, the yoke member mounted to the slide mechanism, and
   the linear measurement assembly includes a read head mounted to the slide mechanism, and a linear encoder scale fixed to the base, the read head operative to move along the linear encoder scale with the slide mechanism.

9. The measurement system of claim 1, wherein the linear measurement assembly includes a linear encoder operative to detect linear motions of the interface assembly.

10. The measurement system of claim 9, wherein the linear encoder includes a movable read head and a fixed scale.

11. The measurement system of claim 10, wherein the linear measurement assembly includes circuitry operative to translate signals from the linear encoder.

12. The measurement system of claim 11, wherein the circuitry is in communication with an output device.

13. The measurement system of claim 12, wherein the output device comprises a visible display.

14. The measurement system of claim 13, wherein the visible display comprises an LED display.

15. The measurement system of claim 12, wherein the output device comprises a printer.

16. The measurement system of claim 9, wherein the linear measurement assembly includes circuitry in communication with a computer.

17. The measurement system of claim 1, wherein the interface assembly further includes a three-axis motion assembly configured to move the optical axis in three orthogonal directions.

18. The measurement system of claim 1, wherein the linear measurement assembly is operative to determine distances to 0.01 mm.

19. A measurement system for measuring distances in an anterior chamber of an eye, comprising:
   a three-axis motion assembly;
   an optical microscope assembly mounted on the motion assembly;
   a controller assembly operative to control motion of the three-axis motion assembly in a first horizontal direction parallel to an optical axis of an eye of a patient, in a second horizontal direction orthogonal to the first horizontal direction to align the microscope assembly with both eyes, and in a vertical direction;
   the controller assembly further operative to determine a distance traveled by the optical microscope assembly in the first horizontal direction; and
   an image recording device optically aligned with the optical microscope assembly to record images from the optical microscope assembly.

20. The measurement system of claim 19, wherein the image recording device includes a camera.

21. The measurement system of claim 20, wherein the image recording device includes a digital camera.

22. The measurement system of claim 19, wherein the image recording device includes a display.

23. The measurement system of claim 19, wherein the display comprises a monitor.

24. The measurement system of claim 19, wherein the display comprises a television monitor.

25. The measurement system of claim 19, wherein the three-axis motion assembly comprises a first horizontal motor stage operative to move in the first horizontal direction, a second horizontal motor stage operative to move in the second horizontal direction, and a vertical motor stage operative to move in the vertical direction.

26. The measurement system of claim 25, wherein each of the first horizontal motor stage, the second horizontal motor stage, and the vertical motor stage includes a step motor operative to advance and retract the associated motor stage in determined increments.

27. The measurement system of claim 19, wherein the controller assembly comprises a computer.

28. The measurement system of claim 27, wherein the computer includes a clock, and the three-axis motion assembly and the image recording device are synchronized with the clock.

29. The measurement system of claim 19, wherein the three-axis motion assembly is operative to move in determined steps under control of the controller assembly, and the image recording system is operative in synchronization with the steps to record an image frame for each step.

30. The measurement system of claim 19, wherein the controller assembly is operative to move the optical microscope between a position focused on a cornea and a position focused on an iris.

31. The measurement system of claim 19, wherein the controller assembly is operative to move the optical microscope between a position focused on an cornea and a position focused on a retina.

32. The measurement system of claim 19, wherein the three-axis motion assembly is mounted on a slit lamp examination table.

33. The measurement system of claim 32, further comprising an engagement mechanism configured to removably latch the three-axis motion assembly into position for use with a slit lamp microscope.

34. The measurement system of claim 32, wherein the three-axis motion assembly is mounted on a side of the slit lamp microscope, and further includes an optical path having a fold therein to transmit light from an optical axis of the eye to an optical axis of the microscope assembly.

35. The measurement system of claim 34, wherein the optical path includes a mirror arranged to provide the fold.

36. The measurement system of claim 34, wherein the fold comprises a right angle bend in the optical path.

37. A process for measuring distances in an anterior chamber of an eye comprising:
   providing a measurement system mounted on a slit lamp examination table for use in conjunction with a slit lamp ophthalmologic microscope assembly, the measurement system comprising:
      a linearly movable interface assembly operative to pick up motions of the microscope assembly in a direction along an optical axis of the eye, and
      a linear measurement assembly coupled to the interface assembly and operative to determine a distance traveled by the interface assembly;
   focusing the microscope assembly on a first location in the eye;
   moving the microscope assembly and the interface assembly along an optical axis of the eye to focus on a second location in the eye; and
   determining the distance traveled by the interface assembly.

38. The process of claim 37, further comprising displaying the distance traveled on a visible display.

39. The process of claim 37, further comprising storing the distance traveled in memory.

* * * * *